United States Patent [19]
Ma et al.

[11] Patent Number: 5,668,164
[45] Date of Patent: Sep. 16, 1997

[54] PROCESS FOR SYNTHESIS OF CHIRAL CIS- AND TRANS-3-AMINO-4 SUBSTITUTED PYRROLIDINE COMPOUNDS

[75] Inventors: Zhenkun Ma; Curt S. Cooper; Anthony K. L. Fung, all of Gurnee, Ill.; Daniel T. Chu, Santa Clara, Calif.

[73] Assignee: Abbott Laboratories, Abbott Park, Ill.

[21] Appl. No.: 764,418

[22] Filed: Dec. 12, 1996

Related U.S. Application Data

[62] Division of Ser. No. 679,043, Jul. 12, 1996, Pat. No. 5,618,949.

[51] Int. Cl.$^6$ .................................................. C07D 413/06
[52] U.S. Cl. .................................................. 514/376; 548/230
[58] Field of Search ................................ 548/230; 514/376

[56] References Cited

PUBLICATIONS

Williams, R. M., et al., "Asymmetric Synthesis of S–(–)–Cucurbitine", Tetrahedron Letters, vol. 33, No. 45, pp. 6735–6758, 1992.
Rispens, M. T., et al., "Asymmetric 1,3–Dipolar Cycloadditions to 5–(R)–Menthyloxy–2(5H)–Furanone", Tetrahydron: Asymmetry, vol. 5, No. 4, pp. 607–624, 1994.
Fray, A. H., et al., "Diastereoselective Azomethine Ylide Cycloadditions to Unsaturated, Chiral Bicyclic Lactams", Tetrahydron Letters, vol. 33, No. 25, pp. 3575–3578, 1992.
Wee, A. G. H., J. Chem. Soc., Perkin Trans. 1, pp. 1363–1364, 1989.
CA 124: 8797 Improved chiral auxillaries . . . and their use. Davies et al. Jul. 1995.

*Primary Examiner*—Joseph K. McKane
*Attorney, Agent, or Firm*—Mona Anand

[57] ABSTRACT

Process for preparation of chiral cis-3,4-substituted pyrrolidine compounds having the formulas:

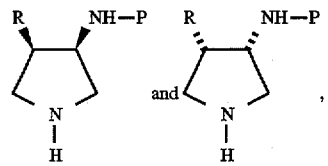

and chiral 3,4-trans-substituted pyrrolidine compounds having the formulas:

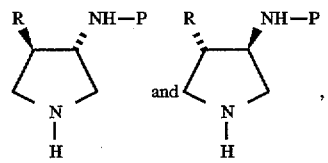

with the assistance of a streochemically directing chiral oxazolidinone moiety having the formula:

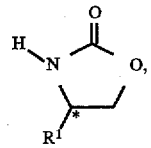

wherein P, R and R$^1$ are specifically defined, by sequential reaction of the compound or subsequent intermediates with an a,b-unsaturated add chloride, reaction with N-benzyl-N-(methoxymethyl)trimethyl-silylmethylamine and separating isomers by chromatography, hydrolytic removal of the oxazolidinone moiety, reaction with diphenylphosphoryl azide and triethylamine, and debenzylating; and novel intermediates of the process.

2 Claims, No Drawings

PROCESS FOR SYNTHESIS OF CHIRAL CIS- AND TRANS-3-AMINO-4 SUBSTITUTED PYRROLIDINE COMPOUNDS

This is a division of U.S. patent application Ser. No. 08/679,043, filed Jul. 12, 1996, now U.S. Pat. No. 5,618,449.

TECHNICAL FIELD

The present invention describes a process for preparing chiral cis- and trans-3-(protected-amino)-4-substituted pyrrolidine compounds having use as intermediates for the preparation of antimicrobial pharmaceutical compounds. The invention also relates to novel intermediate chiral compounds essential to the process.

BACKGROUND OF THE INVENTION

Certain asymmetric 1,3-cycloaddition reactions using N-benzyl-N-(methoxymethyl)trimethylsilylmethylamine (NBNMMA, compound (4) of Scheme 1 below) to produce cis-substitution have been reported. Rispens, et al. (*Tetrahedron: Asymmetry*, 5:607–624 (1994)) disclosed the addition of NBNMMA to 5-(R)-menthyloxy-2(5H)-furanone to produce a cis-fused pyrrolidinofuranone ring system, alleging the use of the latter as a precursor of cis-pyrrolidine compounds. Williams, et al. (*Tetrahedron Lett.*, 33:6755–6758 (1992)) disclosed addition of NBNMMA to an exo-methylene group of a morpholin-2-one compound (an a,b-unsaturated lactone) to produce a spiro-pyrrolidine precursor to S-(–)-cucurbitine. Fray, et al. (*Tetrahedron. Lett.* 33:3575–3578 (1992)) disclosed addition of NBNMMA to non-racemic, unsaturated bicyclic lactams to produce pyrrolidine-cis-fused lactams. Wee (*J. Chem. Soc., Perkin Trans.*, 1:1363–1364 (1989)) disclosed addition of NBNMMA to homochiral a,b-unsaturated esters and lactones to produce cis-substituted pyrrolidine compounds.

However, the use of removable chiral oxazolidinone compounds as auxiliary moieties to assist in stereodirection of NBNMMA in 1,3-cyclo-addition reactions has not been disclosed. It would be desirable to have an improved and efficient process for the preparation of the cis- and trans-3-amino-4-substituted pyrrolidine compounds which may be utilized as intermediates in the preparation of suitably 7-substituted quinolone or 8-substituted 2-pyridone antibiotic compounds represented by the formula:

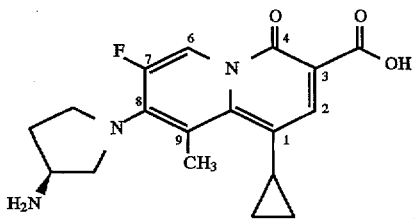

wherein the substitutent 3-aminopyrrolidine at the 8-position exemplifies the chiral 3-aminopyrrolidine substituent at the 8-position.

SUMMARY OF THE INVENTION

The process of the invention is an asymmetric 1,3-dipolar cycloaddition reaction which progresses from a,b-unsaturated acids through novel chiral oxazolidinone intermediates to a convergent synthesis of the desired chiral cis- and trans-substituted pyrrolidines. More specifically, the reaction involves 1,3-cycloaddition of azomethine ylides derived from N-benzyl-N-(methoxymethyl)-trimethylsilylmethylamine.

In one aspect, the present invention is a process for the preparation of chiral 3,4-substituted pyrrolidine compounds, including chiral cis-3,4-substituted pyrrolidine compounds having the formulas:

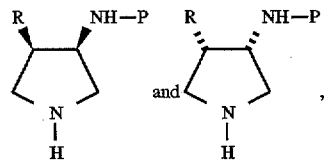

and chiral 3,4-trans-substituted pyrrolidine compounds having the formulas:

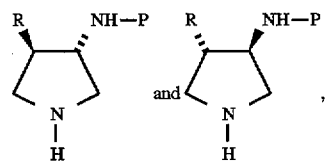

wherein P is a protecting moiety selected from the group consisting of t-butyloxycarbonyl (BOC), benzyloxcarbonyl (CBZ), p-methoxybenzyloxycarbonyl and p-chlorobenzyloxycarbonyl, and R is selected from the group consisting of $C_1$–$C_6$-alkyl, $C_3$–$C_5$-cycloalkyl, phenyl and phenyl-substituted-$C_1$–$C_6$-alkyl; the method comprising:

(a) reacting a chiral oxazolidinone having the formula:

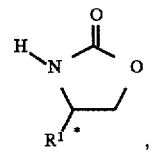

wherein * represents the chiral center and $R^1$ is a sterically controlling moiety selected from the group consisting of isopropyl, isobutyl, t-butyl, phenyl, benzyl, 1-phenylethyl, diphenylmethyl, naphthyl and adamantyl, with a strong base selected from the group consisting of an alkali metal, an alkali metal hydride and an alkali metal-alkyl compound in an aprotic solvent and at −78° C. to −50° C. under an inert atmosphere, followed immediately by addition of a cis-a,b-unsaturated acid chloride having the formula:

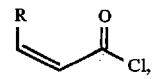

wherein R is as defined above, when cis-compounds are being prepared; or by addition of a trans-a,b-unsaturated acid chloride having the formula:

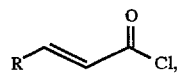

when trans-compounds are being prepared, wherein R is as defined above; and isolating the first intermediate compound having the formula:

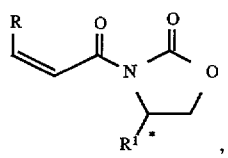

when cis-compounds are being prepared, wherein $R^1$ is as defined above; or isolating the first intermediate compound having the formula:

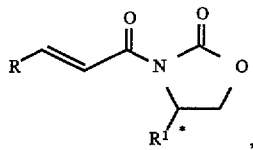

when trans-compounds are being prepared, wherein $R^1$ is as defined above;

(b) condensing the first intermediate compound with N-benzyl-N-(methoxymethyl)trimethylsilylmethylamine in the presence of an acid catalyst, isolating a mixture of second intermediate compounds having the structures:

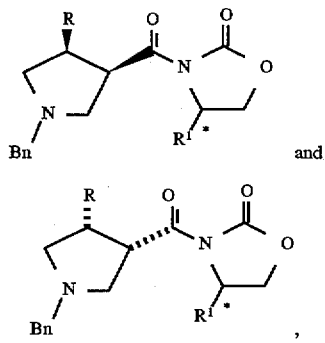

and when cis-compounds are being prepared, or

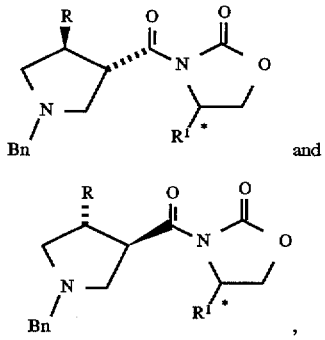

and when trans-compounds are being prepared, which mixture of second intermediate compounds is enriched in one diastereomer over the other depending upon the chirality of the oxazolidinone chiral center, separating the major isomer from the minor isomer by chromatography or recrystallization, and isolating the desired chiral diastereomer of the second intermediate compound, (c) hydrolytically removing the oxazolidine moiety from the second intermediate compound by treatment with LiOH and $H_2O_2$, and isolating the chiral third intermediate compound having the structure:

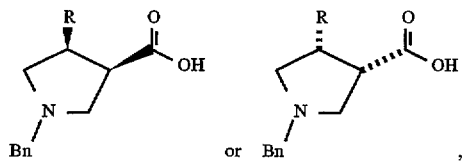

when cis-compounds are being prepared, or

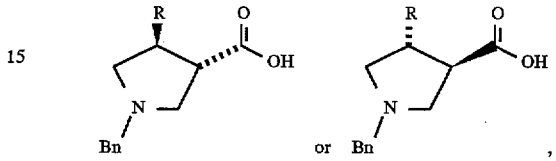

when trans-compounds are being prepared, (d) replacing the carboxyl group of the third intermediate compound with a protected amino group by treatment with diphenylphosphoryl azide and triethylamine in the presence of an alcohol selected from the group consisting of t-butanol, benzyl alcohol, p-methoxybenzyl alcohol and p-chlorobenzyl alcohol to give the chirally appropriate fourth intermediate compound having the structure:

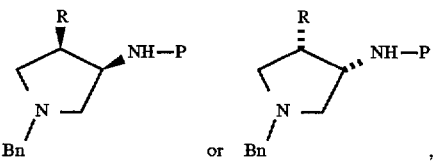

when cis-compounds are being prepared, or

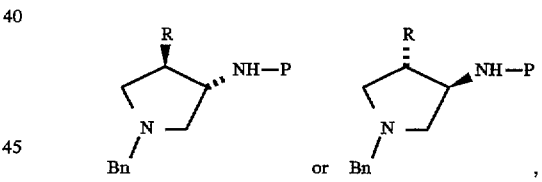

when trans-compounds are being prepared; and (e) debenzylating the pyrrolidine amino group of the fourth intermediate compound by treatment with ammonium formate and Pd/C or $Pd(OH)_2$ catalyst in methanol or by hydrogenation over a Pd/C catalyst, and isolating the desired chiral 3,4-disubstituted product.

The cis- and trans-3-amino-4-substituted pyrrolidine compounds prepared herein can be useful as intermediates in the preparation of suitably 7-substituted quinolone or 8-substituted 2-pyridone antibiotic agents.

Another aspect of the invention relates to novel chiral intermediate compounds essential to the process.

DETAILED DESCRIPTION OF THE INVENTION

In one embodiment of the present invention is a process for the preparation of chiral 3,4-trans-substituted pyrrolidine compounds having the formulas:

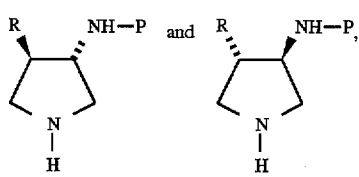 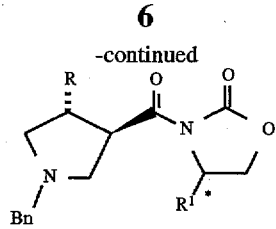

wherein P is a protecting moiety selected from the group consisting of t-butyloxycarbonyl (BOC), benzyloxycarbonyl (CBZ), p-methoxybenzyloxycarbonyl and p-chlorobenzyloxycarbonyl, and R is selected from the group consisting of $C_1$–$C_6$-alkyl, $C_3$–$C_5$-cycloalkyl, phenyl and phenyl-substituted-$C_1$–$C_6$-alkyl, the method comprising:

(a) reacting a chiral oxazolidinone having the formula:

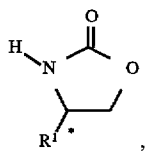

wherein * represents the chiral center and $R^1$ is a sterically controlling moiety selected from the group consisting of isopropyl, isobutyl, t-butyl, phenyl, benzyl, 1-phenylethyl, diphenylmethyl, naphthyl and adamantyl, with a strong base selected from the group consisting of an alkali metal, an alkai metal hydride and an alkyl-alkali metal compound in an aprotic solvent and at −78° C. to −50° C. under an inert atmosphere, followed immediately by addition of a trans-a, b-unsaturated acid chloride having the formula:

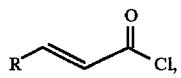

wherein R is as defined above, and isolating the first intermediate compound having the formula:

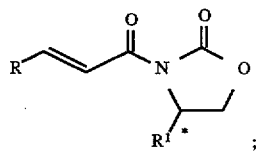

(b) condensing the first intermediate product with N-benzyl-N-(methoxy-methyl) trimethylsilylmethylamine in the presence of an acid catalyst, and isolating a mixture of second intermediate compounds having the structures:

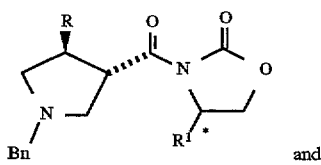 and which mixture of second intermediate compounds is enriched in one diastereomer over the other depending upon the chirality of the chiral center, separating the major isomer from the minor isomer by chromatography or recrystallization, and isolating the desired chiral diastereomer of the second intermediate compound, (c) hydrolytically removing the oxazolidine moiety from the second intermediate by treatment with LiOH and $H_2O_2$, and isolating the chiral third intermediate compound having the structure:

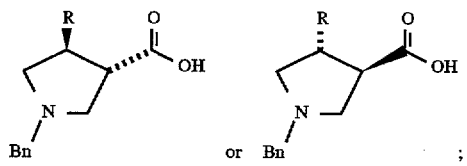

(d) replacing the carboxyl group of the third intermediate compound with a protected amino group by treatment with diphenylphosphoryl azide and triethylamine in the presence of an alcohol selected from the group consisting of t-butanol, benzyl alcohol, p-methoxybenzyl alcohol and p-chlorobenzyloxycarbonyl to give the chirally appropriate fourth intermediate compound having the structure:

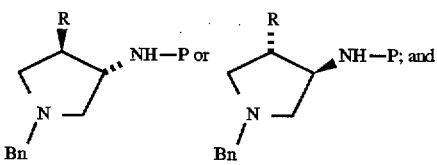

(e) debenzylating the pyrrolidine amino group of the third intermediate compound by treatment with ammonium formate and Pd/C or Pd(OH)$_2$ catalyst in methanol or hydrogenation over a Pd/C catalyst, and isolating the desired chiral trans-3,4-disubstituted product.

In a preferred embodiment of the present invention is a process for the preparation of chiral 3,4-trans-substituted pyrrolidine compounds having the formulas:

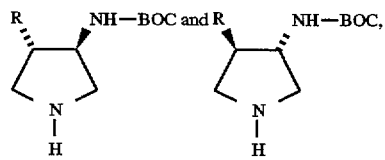

wherein R is $C_1$–$C_6$-alkyl or $C_3$–$C_5$-cycloalkyl, the method comprising:

(a) reacting a chiral oxazolidinone having the formula:

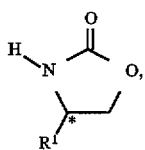

wherein * represents the chiral center and $R^1$ is a sterically controlling moiety selected from the group consisting of isopropyl, phenyl and benzyl, with a strong base selected from the group consisting of an alkali metal and an alkyl-alkali metal compound in an aprotic solvent and at −78° C. to −50° C. under an inert atmosphere, followed immediately by addition of a trans-a,b-unsaturated acid chloride having the formula:

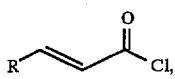

wherein R is as defined above, and isolating the first intermediate compound having the formula:

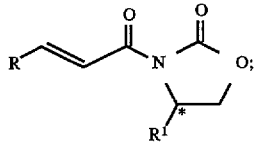

(b) condensing the first intermediate product with N-benzyl-N-(methoxymethyl)trimethylsilylmethylamine in the presence of an acid catalyst, and isolating a mixture of second intermediate compounds having the structures:

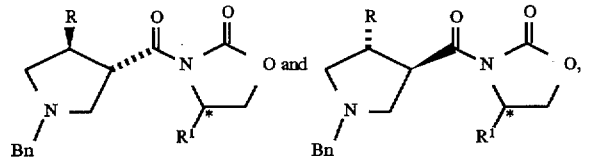

which mixture of second intermediate compounds is enriched in one diastereomer over the other depending upon the chirality of the chiral center, separating the major isomer from the minor isomer by chromatography or recrystallization, and isolating the desired chiral diastereomer of the second intermediate compound, (c) hydrolyrically removing the oxazolidine moiety from the second intermediate by treatment with LiOH and $H_2O_2$, and isolating the chiral third intermediate compound having the structure:

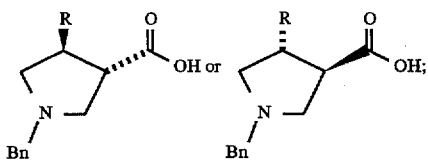

(d) replacing the carboxyl group of the third intermediate compound with a BOC-protected amino group by treatment with diphenylphosphoryl azide and triethylamine in t-butanol to give the chirally appropriate fourth intermediate compound having the structure:

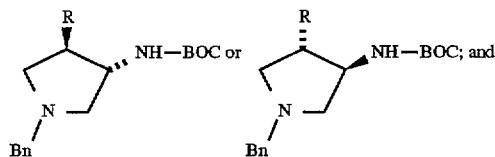

(e) debenzylating the pyrrolidine amino group of the third intermediate compound by treatment with ammonium formate and Pd/C or Pd(OH)$_2$ catalyst in methanol or hydrogenation over a Pd/C catalyst, and isolating the desired chiral trans-3,4-disubstituted product.

In another embodiment of the present invention is a process for the preparation of chiral 3,4-cis-substituted pyrrolidine compounds having the formulas:

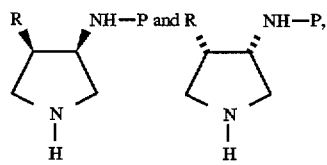

wherein P is a protecting moiety selected from the group consisting of t-butyloxycarbonyl (BOC), benzyloxcarbonyl (CBZ), p-methoxybenzyloxycarbonyl and p-chlorobenzyloxycarbonyl, and R is selected from the group consisting of $C_1$-$C_6$-alkyl, $C_3$-$C_5$-cycloalkyl, phenyl and phenyl-substituted-$C_1$-$C_6$-alkyl, the method comprising:

(a) reacting a chiral oxazolidinone having the formula:

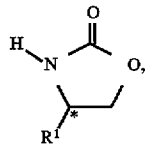

wherein * represents the chiral center and $R^1$ is a sterically controlling moiety selected from the group consisting of isopropyl, isobutyl, t-butyl, phenyl, benzyl, 1-phenylethyl, diphenylmethyl, naphthyl and adamantyl, with a strong base selected from the group consisting of an alkali metal and an alkyl-alkali metal compound in an aprotic solvent and at −78° C. to −50° C. under an inert atmosphere, followed immediately by addition of a cis-a,b-unsaturated acid chloride having the formula:

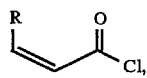

wherein R is as defined above, and isolating the first intermediate compound having the formula:

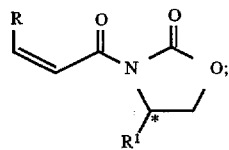

(b) condensing the first intermediate product with N-benzyl-N-(methoxymethyl) trimethylsilylmethylamine in the presence of an acid catalyst, and isolating a mixture of second intermediate compounds having the structures:

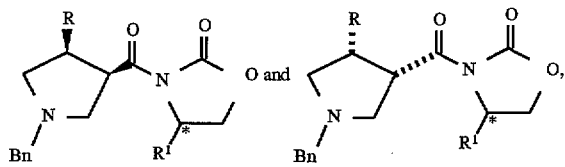

which mixture of second intermediate compounds is enriched in one diastereomer over the other depending upon the chirality of the chiral center, separating the major isomer from the minor isomer by chromatography or recrystallization, and isolating the desired chiral diastereomer of the second intermediate compound (c) hydrolytically removing the oxazolidine moiety from the second intermediate by treatment with LiOH and $H_2O_2$, and isolating the chiral third intermediate compound having the structure:

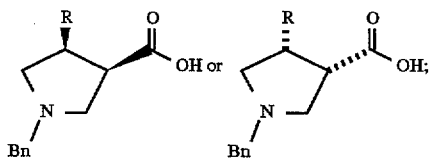

(d) replacing the carboxyl group of the third intermediate compound with a protected amino group by treatment with diphenylphosphoryl azide and triethylamine in the presence of an alcohol selected from the group consisting of t-butanol, benzyl alcohol, p-methoxybenzyl alcohol and p-chlorobenzyl alcohol to give the chirally appropriate fourth intermediate compound having the structure:

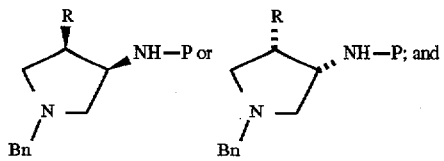

(e) debenzylating the pyrrolidine amino group of the third intermediate compound by treatment with ammonium formate and Pd/C or Pd(OH)$_2$ catalyst in methanol or hydrogenation over a Pd/C catalyst, and isolating the desired chiral cis-3,4-disubstituted product.

In another preferred embodiment of the present invention is a process for the preparation of chiral 3,4-cis-substituted pyrrolidine compounds having the formulas:

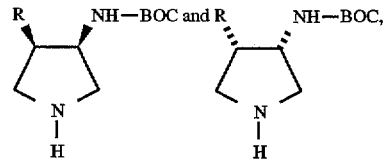

wherein R is $C_1$–$C_6$-alkyl or $C_3$–$C_5$-cycloalkyl, the method comprising:

(a) reacting a chiral oxazolidinone having the formula:

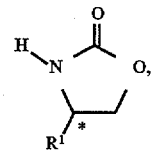

wherein * represents the chiral center and $R^1$ is a sterically controlling moiety selected from the group consisting of isopropyl, phenyl and benzyl, with a strong base selected from the group consisting of an alkali metal and an alkyl-alkali metal compound in an aprotic solvent and at –78° C. to –50° C. under an inert atmosphere, followed immediately by addition of a cis-a,b-unsaturated acid chloride having the formula:

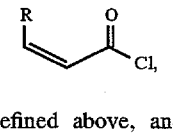

wherein R is as defined above, and isolating the first intermediate compound having the formula:

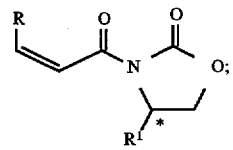

(b) condensing the first intermediate product with N-benzyl-N-(methoxymethyl) trimethylsilylmethylamine in the presence of an acid catalyst, and isolating a mixture of second intermediate compounds having the structures:

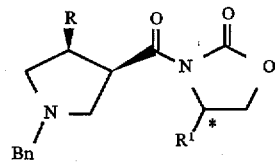

and

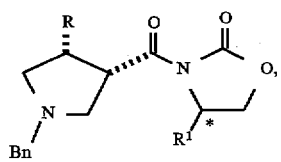

which mixture of second intermediate compounds is enriched in one diastereomer over the other depending upon the chirality of the chiral center, separating the major isomer from the minor isomer by chromatography or recrystallization, and isolating the desired chiral diastereomer of the second intermediate compound, (c) hydrolytically removing the oxazolidine moiety from the second intermediate by treatment with LiOH and $H_2O_2$, and isolating the chiral third intermediate compound having the structure:

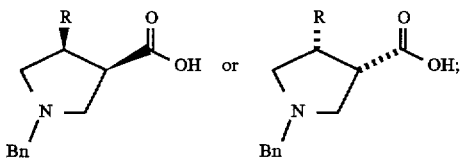

(d) replacing the carboxyl group of the third intermediate compound with a BOC-protected amino group by treatment with diphenylphosphoryl azide and triethylamine in t-butanol to give the chirally appropriate fourth intermediate compound having the structure:

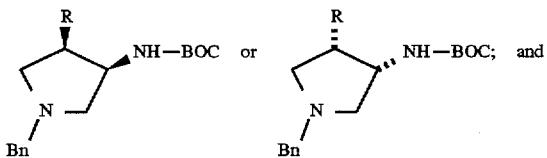

(e) debenzylating the pyrrolidine amino group of the third intermediate compound by treatment with ammonium formate and Pd/C or Pd(OH)$_2$ catalyst in methanol or hydrogenation over a Pd/C catalyst, and isolating the desired chiral cis-3,4-disubstituted product.

In another aspect of the invention are novel intermediate compounds essential to the process described above, said compounds being selected from the group consisting of compounds having the formulas:

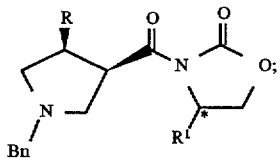 (a)

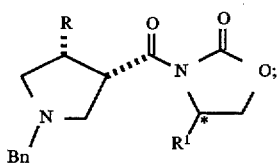 (b)

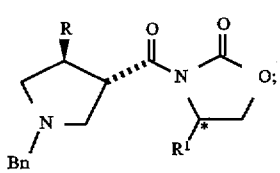 (c)

and

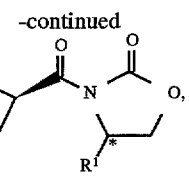 (d)

wherein * represents a chiral center, Bn is benzyl, R is selected from the group consisting of $C_1$-$C_6$-alkyl, $C_3$-$C_5$-cycloalkyl, phenyl and phenyl-substituted-$C_1$-$C_6$-alkyl, and $R^1$ is selected from the group consisting of isopropyl, isobutyl, t-butyl, phenyl, benzyl, 1-phenylethyl, diphenylmethyl, naphthyl and adamantyl.

Representative intermediate compounds include:
3-(trans-1-benzyl-4-(S)-cyclopropyl-3-(S)-pyrrolidinylcarbonyl)-4-(R)-phenyl-2-oxazolidinone;
3-(trans-1-benzyl-4-(R)-cyclopropyl-3-(R)-pyrrolidinylcarbonyl)-4-(R)-phenyl-2-oxazolidinone;
3-(trans-1-benzyl-4-(S)-cyclopropyl-3-(S)-pyrrolidinylcarbonyl)-4-(S)-phenyl-2-oxazolidinone;
3-(trans-1-benzyl-4-(R)-cyclopropyl-3-(R)-pyrrolidinylcarbonyl)-4-(S)-phenyl-2-oxazolidinone;
3-(trans-1-benzyl-4-(S)-methyl-3-(S)-pyrrolidinylcarbonyl)-4-(R)-phenyl-2-oxazolidinone;
3-(trans-1-benzyl-4-(R)-methyl-3-(R)-pyrrolidinylcarbonyl)-4-(R)-phenyl-2-oxazolidinone;
3-(trans-1-benzyl-4-(S)-methyl-3-(S)-pyrrolidinylcarbonyl)-4-(S)-phenyl-2-oxazolidinone;
3-(trans-1-benzyl-4-(R)-methyl-3-(R)-pyrrolidinylcarbonyl)-4-(S)-phenyl-2-oxazolidinone;
3-(trans-1-benzyl-4-(S)-ethyl-3-(S)-pyrrolidinylcarbonyl)-4-(R)-phenyl-2-oxazolidinone;
3-(trans-1-benzyl-4-(R)-ethyl-3-(R)-pyrrolidinylcarbonyl)-4-(R)-phenyl-2-oxazolidinone;
3-(trans-1-benzyl-4-(S)-ethyl-3-(S)-pyrrolidinylcarbonyl)-4-(S)-phenyl-2-oxazolidinone;
3-(trans-1-benzyl-4-(R)-ethyl-3-(R)-pyrrolidinylcarbonyl)-4-(S)-phenyl-2-oxazolidinone;
3-(trans-1-benzyl-4-(S)-cyclopropyl-3-(S)-pyrrolidinylcarbonyl)-4-(R)-isopropyl-2-oxazolidinone;
3-(trans-1-benzyl-4-(R)-cyclopropyl-3-(R)-pyrrolidinylcarbonyl)-4-(R)-isopropyl-2-oxazolidinone;
3-(trans-1-benzyl-4-(S)-cyclopropyl-3-(S)-pyrrolidinylcarbonyl)-4-(S)-isopropyl-2-oxazolidinone;
3-(trans-1-benzyl-4-(R)-cyclopropyl-3-(R)-pyrrolidinylcarbonyl)-4-(S)-isopropyl-2-oxazolidinone;
3-(trans-1-benzyl-4-(S)-methyl-3-(S)-pyrrolidinylcarbonyl)-4-(R)-isopropyl-2-oxazolidinone;
3-(trans-1-benzyl-4-(R)-methyl-3-(R)-pyrrolidinylcarbonyl)-4-(R)-isopropyl-2-oxazolidinone;
3-(trans-1-benzyl-4-(S)-methyl-3-(S)-pyrrolidinylcarbonyl)-4-(S)-isopropyl-2-oxazolidinone;
3-(trans-1-benzyl-4-(R)-methyl-3-(R)-pyrrolidinylcarbonyl)-4-(S)-isopropyl-2-oxazolidinone;
3-(trans-1-benzyl-4-(S)-ethyl-3-(S)-pyrrolidinylcarbonyl)-4-(R)-isopropyl-2-oxazolidinone;
3-(trans-1-benzyl-4-(R)-ethyl-3-(R)-pyrrolidinylcarbonyl)-4-(R)-isopropyl-2-oxazolidinone;
3-(trans-1-benzyl-4-(S)-ethyl-3-(S)-pyrrolidinylcarbonyl)-4-(S)-isopropyl-2-oxazolidinone;
3-(trans-1-benzyl-4-(R)-ethyl-3-(R)-pyrrolidinylcarbonyl)-4-(S)-isopropyl-2-oxazolidinone;
3-(trans-1-benzyl-4-(S)-cyclopropyl-3-(S)-pyrrolidinylcarbonyl)-4-(R)-benzyl-2-oxazolidinone;
3-(trans-1-benzyl-4-(R)-cyclopropyl-3-(R)-pyrrolidinylcarbonyl)-4-(R)-benzyl-2-oxazolidinone;
3-(trans-1-benzyl-4-(S)-cyclopropyl-3-(S)-pyrrolidinylcarbonyl)-4-(S)-benzyl-2-oxazolidinone;

3-(trans-1-benzyl-4-(R)-cyclopropyl-3-(R)-pyrrolidinylcarbonyl)-4-(S)-benzyl-2-oxazolidinone;
3-(trans-1-benzyl-4-(S)-methyl-3-(S)-pyrrolidinylcarbonyl)-4-(R)-benzyl-2-oxazolidinone;
3-(trans-1-benzyl-4-(R)-methyl-3-(R)-pyrrolidinylcarbonyl)-4-(R)-benzyl-2-oxazolidinone;
3-(trans-1-benzyl-4-(S)-methyl-3-(S)-pyrrolidinylcarbonyl)-4-(S)-benzyl-2-oxazolidinone;
3-(trans-1-benzyl-4-(R)-methyl-3-(R)-pyrrolidinylcarbonyl)-4-(S)-benzyl-2-oxazolidinone;
3-(trans-1-benzyl-4-(S)-ethyl-3-(S)-pyrrolidinylcarbonyl)-4-(R)-benzyl-2-oxazolidinone;
3-(trans-1-benzyl-4-(R)-ethyl-3-(R)-pyrrolidinylcarbonyl)-4-(R)-benzyl-2-oxazolidinone;
3-(trans-1-benzyl-4-(S)-ethyl-3-(S)-pyrrolidinylcarbonyl)-4-(S)-benzyl-2-oxazolidinone;
3-(trans-1-benzyl-4-(R)-ethyl-3-(R)-pyrrolidinylcarbonyl)-4-(S)-benzyl-2-oxazolidinone;
3-(cis-1-benzyl-4-(S)-cyclopropyl-3-(R)-pyrrolidinylcarbonyl)-4-(R)-phenyl-2-oxazolidinone;
3-(cis-1-benzyl-4-(R)-cyclopropyl-3-(S)-pyrrolidinylcarbonyl)-4-(R)-phenyl-2-oxazolidinone;
3-(cis-1-benzyl-4-(S)-cyclopropyl-3-(R)-pyrrolidinylcarbonyl)-4-(S)-phenyl-2-oxazolidinone;
3-(cis-1-benzyl-4-(R)-cyclopropyl-3-(S)-pyrrolidinylcarbonyl)-4-(S)-phenyl-2-oxazolidinone;
3-(cis-1-benzyl-4-(S)-methyl-3-(R)-pyrrolidinylcarbonyl)-4-(R)-phenyl-2-oxazolidinone;
3-(cis-1-benzyl-4-(R)-methyl-3-(S)-pyrrolidinylcarbonyl)-4-(R)-phenyl-2-oxazolidinone;
3-(cis-1-benzyl-4-(S)-methyl-3-(R)-pyrrolidinylcarbonyl)-4-(S)-phenyl-2-oxazolidinone;
3-(cis-1-benzyl-4-(R)-methyl-3-(S)-pyrrolidinylcarbonyl)-4-(S)-phenyl-2-oxazolidinone;
3-(cis-1-benzyl-4-(S)-ethyl-3-(R)-pyrrolidinylcarbonyl)-4-(R)-phenyl-2-oxazolidinone;
3-(cis-1-benzyl-4-(R)-ethyl-3-(S)-pyrrolidinylcarbonyl)-4-(R)-phenyl-2-oxazolidinone;
3-(cis-1-benzyl-4-(S)-ethyl-3-(R)-pyrrolidinylcarbonyl)-4-(S)-phenyl-2-oxazolidinone;
3-(cis-1-benzyl-4-(R)-ethyl-3-(S)-pyrrolidinylcarbonyl)-4-(S)-phenyl-2-oxazolidinone;
3-(cis-1-benzyl-4-(S)-cyclopropyl-3-(R)-pyrrolidinylcarbonyl)-4-(R)-isopropyl-2-oxazolidinone;
3-(cis-1-benzyl-4-(R)-cyclopropyl-3-(S)-pyrrolidinylcarbonyl)-4-(R)-isopropyl-2-oxazolidinone;
3-(cis-1-benzyl-4-(S)-cyclopropyl-3-(R)-pyrrolidinylcarbonyl)-4-(S)-isopropyl-2-oxazolidinone;
3-(cis-1-benzyl-4-(R)-cyclopropyl-3-(S)-pyrrolidinylcarbonyl)-4-(S)-isopropyl-2-oxazolidinone;
3-(cis-1-benzyl-4-(S)-methyl-3-(R)-pyrrolidinylcarbonyl)-4-(R)-isopropyl-2-oxazolidinone;
3-(cis-1-benzyl-4-(R)-methyl-3-(S)-pyrrolidinylcarbonyl)-4-(R)-isopropyl-2-oxazolidinone;
3-(cis-1-benzyl-4-(S)-methyl-3-(R)-pyrrolidinylcarbonyl)-4-(S)-isopropyl-2-oxazolidinone;
3-(cis-1-benzyl-4-(R)-methyl-3-(S)-pyrrolidinylcarbonyl)-4-(S)-isopropyl-2-oxazolidinone;
3-(cis-1-benzyl-4-(S)-ethyl-3-(R)-pyrrolidinylcarbonyl)-4-(R)-isopropyl-2-oxazolidinone;
3-(cis-1-benzyl-4-(R)-ethyl-3-(S)-pyrrolidinylcarbonyl)-4-(R)-isopropyl-2-oxazolidinone;
3-(cis-1-benzyl-4-(S)-ethyl-3-(R)-pyrrolidinylcarbonyl)-4-(S)-isopropyl-2-oxazolidinone;
3-(cis-1-benzyl-4-(R)-ethyl-3-(S)-pyrrolidinylcarbonyl)-4-(S)-isopropyl-2-oxazolidinone;
3-(cis-1-benzyl-4-(S)-cyclopropyl-3-(R)-pyrrolidinylcarbonyl)-4-(R)-benzyl-2-oxazolidinone;
3-(cis-1-benzyl-4-(R)-cyclopropyl-3-(S)-pyrrolidinylcarbonyl)-4-(R)-benzyl-2-oxazolidinone;
3-(cis-1-benzyl-4-(S)-cyclopropyl-3-(R)-pyrrolidinylcarbonyl)-4-(S)-benzyl-2-oxazolidinone;
3-(cis-1-benzyl-4-(R)-cyclopropyl-3-(S)-pyrrolidinylcarbonyl)-4-(S)-benzyl-2-oxazolidinone;
3-(cis-1-benzyl-4-(S)-methyl-3-(R)-pyrrolidinylcarbonyl)-4-(R)-benzyl-2-oxazolidinone;
3-(cis-1-benzyl-4-(R)-methyl-3-(S)-pyrrolidinylcarbonyl)-4-(R)-benzyl-2-oxazolidinone;
3-(cis-1-benzyl-4-(S)-methyl-3-(R)-pyrrolidinylcarbonyl)-4-(S)-benzyl-2-oxazolidinone;
3-(cis-1-benzyl-4-(R)-methyl-3-(S)-pyrrolidinylcarbonyl)-4-(S)-benzyl-2-oxazolidinone;
3-(cis-1-benzyl-4-(S)-ethyl-3-(R)-pyrrolidinylcarbonyl)-4-(R)-benzyl-2-oxazolidinone;
3-(cis-1-benzyl-4-(R)-ethyl-3-(S)-pyrrolidinylcarbonyl)-4-(R)-benzyl-2-oxazolidinone;
3-(cis-1-benzyl-4-(S)-ethyl-3-(R)-pyrrolidinylcarbonyl)-4-(S)-benzyl-2-oxazolidinone; and
3-(cis-1-benzyl-4-(R)-ethyl-3-(S)-pyrrolidinylcarbonyl)-4-(S)-benzyl-2-oxazolidinone.

ABBREVIATIONS

Abbreviations which have been used in the descriptions of the scheme and the examples that follow are: AcOEt for ethyl acetate; t-BuOH for t-butanol; DMF for dimethyl formamide; MeOH for methanol; THF for tetrahydrofuran.

SYNTHETIC METHODS

The processes of the invention may be better understood by reference to the reaction scheme illustrated below.

SCHEME 1

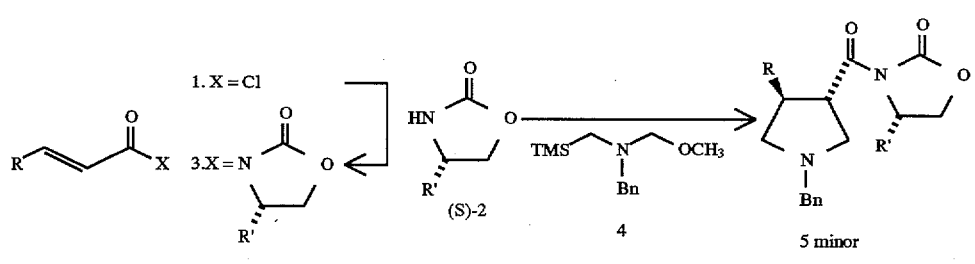

-continued
SCHEME 1

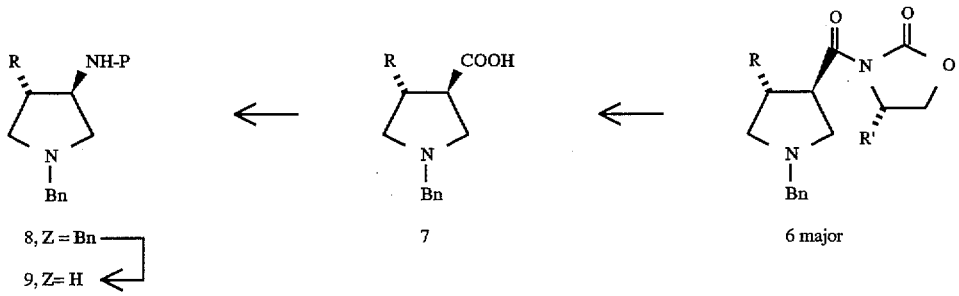

In accordance with Scheme 1, dipolarophiles 3 are easily prepared by coupling a trans-a,b-unsaturated acid chloride (prepared from the precursor acid by treatment with oxalyl chloride and DMF at ambient temperature) and a chiral oxazolidinone (illustrated by the chiral (S) compound) 2. This coupling reaction may be performed in an aprotic solvent such as THF by activation of compound 2 with an alkali metal, an alkali metal hydride, an alkyllithium or other alkali metal alkyl at −78° C. to −50° C. under an inert atmosphere. The oxazolidinone group serves two purposes; as chiral control element and as activator of the unreactive a,b-unsaturated acid. Since there is a wide availability of a,b-unsaturated acids, a broad array of dipolarophiles with different R groups may be easily obtained.

Reaction of 3 with N-benzyl-N-(methoxymethyl) trimethylsilylmethylamine 4 is catalyzed by trifluoroacetic acid and may be performed in an appropriate solvent such as toluene, for example at from 0° C. to ambient temperature, to prepare the diastereomeric pyrrolidines 5 and 6. The diastereoselectivity depends both on the structure of the chiral auxiliaries and upon the reaction conditions, and the desired isomer may be separated easily from the diastereomeric mixture by flash chromatography (silica gel, with, for example, AcOEt:Hexane 1:2) or by recrystallization.

Compound 6 is hydrolyzed with LiOH and $H_2O_2$ in aqueous THF at ambient temperature to afford compound 7. Compound 7 is converted into compound 8, wherein P is a protecting group, by treatment with diphenylphosphoryl azide and triethylamine in the presence of an alcohol such as, for example, t-butanol, benzyl alcohol, p-methoxybenzyl alcohol and p-chlorophenol, at 100° C. Hydrogenolytic removal of the benzyl group is accomplished by treatment with $HCO_2NH_4$ and 10% Pd—C, in MeOH at reflux to give compound 9 in high yield.

Both enantiomers of the pyrrolidines may be obtained by using the appropriate chiral oxazolidinones. Also this process may be used for large scale synthesis.

The absolute stereochemistry of the major product obtained from Example 2 has been determined by single X-ray crystallography. This compound possessed an (3R, 4R) configuration on the pyrrolidine ring as shown by structure 6 (R=cyclopropyl, R'=phenyl).

In the case wherein the process described in Scheme 1 is performed upon an alternate starting material which is a cis-a,b-unsaturated acid compound analogous to compound 1, then cis-enantiomeric products analogous to compounds 8 and 9 may be obtained.

EXAMPLES

The invention may be better understood by reference to the following examples, which are provided for the illustration and not limitation of the invention. Chemists skilled in the art will be able, without undue experimentation, to determine optimum reaction conditions selective for higher diastereoselectivity or yield of the processes.

Example 1

Preparation of (3S,4S)-trans-4-cyclopropyl-3-(BOC-amino)pyrrolidine via use of (R)-(−)-4-phenyl-2-oxazolidinone as chiral control agent 1a. rans-3-cyclopropyl-2-propenoic acid Cyclopropanecarboxaldehyde (50 g, 0.710 mmol, Aldrich) and malonic acid (78 g, 0.750 mmol) were dissolved in pyridine (80 mL, 994 mmol), and the reaction mixture was heated to 100° C. under $N_2$ for 6 hours and cooled to room temperature. The solution was adjusted to pH 1 by addition of 10% $H_2SO_4$ (600 mL), and cooled to 0° C. The product was filtered and washed with water (54.9 g, 69% yield). MS m/z 130 $(M+NH_4)^+$.

1b. trans-3-cydopropyl-2-propenoyl chloride

The compound from step 1a (30.91 g, 0.276 mmol) was dissolved in toluene (400 mL), and the solution was cooled to 0° C. and flushed with $N_2$. Oxalyl chloride (70.06 g, 0.552 mmol) was added dropwise over 20 minutes, followed by addition of anhydrous DMF (0.200 mL). The mixture was stirred at 0° C. for 1 hour and at room temperature for 3 hours. The volatiles were removed under vacuum to give the title compound.

1c. 3-(trans-3-cyclopropyl-2-propenoyl)-4-(R)-phenyl-2-oxazolidinone (R)-(−)-4-Phenyl-2-oxazolidinone (39.12 g, 0.240 mmol, Aldrich) was dissolved in THF (600 mL), and the solution was cooled to −78° C. and flushed with $N_2$. n-Butyllithium (2.5M in THF, 96.0 mL, 0.240 mmol) was introduced over 25 minutes. The compound from step 1b (0.276 mmol) was added while maintaining the temperature at −78° C., and the mixture was stirred at this temperature for half an hour. The mixture was stirred as it was allowed to warm to room temperature. Saturated aqueous $NH_4Cl$ solution was added, the mixture was stirred for 10 minutes and the THF was removed under reduced pressure. The residue was dissolved in ethyl acetate, and the solution was washed with water, 5% aqueous $NaHCO_3$ and brine, then dried over $Na_2SO_4$. The solvent was removed to afford the title compound, which was recrystallized from ethyl acetate:hexane to give the title product (54.660 g, 89% yield). MS m/z 258 $(M+H)^+$, 275 $(M+NH_4)^+$.

1d. 3-(trans-1-benzyl-4-(S)-cyclopropyl-3-(S)-pyrrolidinylcarbonyl)-4-(R)-phenyl-2-oxazolidinone The compound from step 1c (51.40 g, 0.200 mol) was dissolved in toluene (800 mL), and the solution was cooled to 0° C. and flushed with $N_2$. N-Benzyl-N-(methoxymethyl) trimethylsilylmethylamine (56.88 g, 0.240 mmol) was added via a syringe, and the mixture was stirred for 20 minutes. Trifluoroacetic acid (1M, 20.0 mL, 0.020 mmol) was added dropwise over 20 minutes with stirring and at 0° C. The mixture was stirred for 6 hours, then washed with 5% aqueous $NaHCO_3$ and brine, then dried over $Na_2SO_4$. The solution was allowed to stand overnight in a freezer. The product was filtered, then recrystallized from ethyl acetate-:hexane to give the title compound. A second crop was recovered by flash chromatography of the filtrate on silica gel by eluting with a gradient of 1:1:2 methylene chloride-:ethyl acetate:hexane to 1:1 ethyl acetate hexane. The major isomer was taken to the next step.

The (3S, 4S) isomer 61.20 g (78%): MS m/z 391 (M+H)$^+$. NMR (CDCl$_3$) d 7.20–7.40 (10H, m), 5.43 (1H, dd, J=9.0, 4.5 Hz), 4.69 (1H, t, d=9.3), 4.23 (1H, dd, J=9.0, 4.5 Hz), 3.98 (1H, m), 3.65 (1H, d, J=13.5 Hz), 3.44 (1H, d, J=13.5 Hz), 3.03 (1H, dd, J=9.3, 9.0 Hz), 2.84 (1H, dd, J=9.0, 8.4 Hz), 2.64 (1H, dd, J=10.2, 6.0 Hz), 2.36 (1H, dd, J=9.0, 5.2 Hz), 2.08 (1H, m), 0.77 (1H, m), 0.40 (2H, m), 0.09 (1H, m).

The (3R, 4R) isomer 15.63 g (20%): MS m/z 391 (M+H)$^+$. NMR (CDCl$_3$) d 7.20–7.40 (10H, m), 5.42 (1H, dd, J=9.0, 4.5 Hz), 4.66 (1H, t, d=9.0), 4.26 (1H, dd, J=9.0, 4.5 Hz), 4.10 (1H, m), 3.66 (1H, d, J=12.9 Hz), 3.55 (1H, d, J=12.9 Hz), 3.01 (1H, dd, J=9.3, 9.0 Hz), 2.87 (1H, dd, J=9.0, 8.4 Hz), 2.69 (1H, dd, J=9.6, 6.3 Hz), 2.41 (1H, dd, J=9.0, 7.8 Hz), 1.90 (1H, m), 0.75 (1H, m), 0.34 (1H, m), 0.25 (1H, m), –0.02 (1H, m).

1e. (3S,4S)-trans-1-benzyl-4-cyclopropyl-3-pyrrolidinecarboxylic acid

The major isomer of the compound of step 1d (58.50 g, 0.150 mmol) was dissolved in THF, and the solution was cooled to 0° C. LiOH monohydrate (15.75 g, 0.375 mmol) was dissolved in water, $H_2O_2$ (30%, 34.00 mL, 0.300 mmol) was added, and the solution was added dropwise to the THF solution of the starting material over 30 minutes. The mixture was stirred for 1 hour, then diluted with water (800 mL). To this was added sodium sulfite (37.8 g, 0.300 mmol), and the mixture was extracted with ethyl acetate. The aqueous phase was adjusted to pH 4.6 with $NaH_2PO_4$ (68 g, 0.50 mmol) and 10% HCl, then saturated with NaCl (200 g). This solution was extracted with 1:3 isopropyl alcohol:methylene chloride, which was washed with brine, dried over $Na_2SO_4$ and evaporated to dryness to afford the title compound (37.0 g). MS m/z 246 (M+H)$^+$.

1f. (3S,4S)-trans-1-benzyl-4-cyclopropyl-3-(BOC-amino) pyrrolidine

The compound from step 1e (37.00 g, 0.150 mmol) was dissolved in t-butanol, and the solution was flushed with $N_2$. Triethylamine (30.35 g, 0.300 mmol) and diphenylphosphoryl azide (47.47 g, 0.173 mmol) were added via syringe, and the mixture was heated to 95° C. for 72 hours. The solvent was removed under vacuum, and the residue was purified by flash chromatography on silica gel to afford the title compound (37.86 g). MS m/z 317 (M+H)$^+$.

1g. (3S,4S)-trans-4-cyclopropyl-3-(BOC-amino)pyrrolidine

The compound from step 1f (37.86 g, 0.105 mol) was dissolved in methanol (400 mL), the solution was flushed with $N_2$, and 10% Pd/C (1.6 g) and ammonium formate (36.0 g, 0.57 mol) were added. The mixture was heated at 80° C. for 5 hours, cooled, diluted with methylene chloride, filtered and concentrated to give the title compound (31.13 g). MS m/z 227 (M+H)$^+$. NMR (CDCl$_3$) d 4.15 (1H, m), 3.38 (2H, m), 3.14 (1H, m), 2.94 (1H, m), 1.22 (1H, m), 1.43 (9H, s), 0.65 (1H, m), 0.53 (2H, m), 0.33 (1H, m), 0.14 (1H, m).

Example 2

Preparation of (3R,4R)-trans-4-cyclopropyl-3-(BOC-amino)pyrrolidine via use of (S)-(+)-4-phenyl-2-oxazolidinone as chiral control agent The procedure of Example 1 was repeated, except substituting (S)-(–)-4-phenyl-2-oxazolidinone for the (S)-(–)-4-phenyl-2-oxazolidinone of Example 1, step c. MS m/z 227 (M+H)$^+$. NMR (CDCl$_3$) d 3.86 (1H, m), 3.10–3.30 (2H, m), 2.65–2.80 (2H, m), 1.24 (1H, m), 1.43 (9H, s), 0.70 (1H, m), 0.48 (2H, m), 0.27 (1H, m), 0.10 (1H, m). The title compound was shown to be the (3R,4R)-isomer by single crystal X-ray crystallography.

Example 3

Preparation of (3R,4R)-trans4-methyl-3-(BOC-amino)pyrrolidine via use of (S)-4-isopropyl-2-oxazolidinone as chiral control agent 3a. 3-(trans-1-benzyl-4-methyl-3-pyrrolidinylcarbonyl)-4-(S)-isopropyl-2-oxazolidinone 3-(trans-3-Methyl-2-propenoyl)-4-(S)-isopropyl-2-oxazolidinone (197 mg, 1.00 mmol, Aldrich) was reacted with N-benzyl-N-(methoxymethyl) trimethylsilylmethylamine (238 mg, 1.00 mmol) according to the procedure of Example 1d, to afford the title compound (300 mg). The diasteromers were separated as in Example 1d, and the (3R,4R)-isomer was taken to the next step. MS m/z 331 (M+H)$^+$. The (3S,4S)-isomer was taken to Example 4. MS m/z 331 (M+H)$^+$.

3b. (3R,4R)-trans-4-methyl-3-(BOC-amino)pyrrolidine

Carrying the compound of step 3b forward according to the procedures of Example 1e–1g, the title compound is prepared.

Example 4

Preparation of (3S,4S)-trans-4-methyl-3-(BOC-amino)pyrrolidine

The (3S,4S)-isomer of 3-(trans-1-benzyl-4-methyl-3-pyrrolidinylcarbonyl)-4-(S)-isopropyl-2-oxazolidinone, obtained from the mixture of Example 3b, is carried forward according to the procedures of Example 1e–1g to prepare the title compound.

Example 5

Preparation of (3S,4S)-trans-4-methyl-3-(BOC-amino)pyrrolidine via use of (R)-4-benzyl-2-oxazolidinone as chiral control agent 5a. 3-(trans-3-methyl-2-propenoyl)-4-(R)-benzyl-2-oxazolidinone trans-Crotonoyl chloride (Aldrich) was coupled with (R)-4-benzyl-2-oxazolidinone according to the procedure of Example 1c to afford the title compound.

5b. 3-(trans-1-benzyl-4-methyl-3-pyrrolidinylcarbonyl)-4-(R)-benzyl-2-oxazolidinone The compound from step 5a (245 mg, 1.00 mmol) was reacted with N-benzyl-N-(methoxymethyl) trimethylsilylmethylamine (254 mg, 1.2 mmol) according to the procedure of Example 1d, to afford the title compound (170 mg). MS m/z 379 (M+H)$^+$. NMR (CDCl$_3$) d 7.15–7.40 (10H, m), 4.69 (1H, m), 4.20 (1H, dd, J=16.5, 9.0 Hz), 4.18 (1H, dd, J=9.0, 6.0 Hz), 3.71 (1H, d, J=13.5 Hz), 3.65 (1H, m), 3.56 (1H, d, J+13.5 Hz), 3.24 (1H, dd, J=13.5, 3.3 Hz), 2.70–3.10 (4H, m), 2.17 (1H, dd, 8.4, 7.5 Hz), 1.08 (3H, d, J=6.9 Hz).

5c. (3S,4S)-trans-4-methyl-3-(BOC-amino)pyrrolidine

Carrying the compound of step 5b forward according to the procedures of Example 1e–1g, the title compound is prepared.

Example 6

Preparation of (3S,4S)-trans-4-methyl-3-(BOC-amino)pyrrolidine via use of (R)-4-phenyl-2-oxazolidinone as chiral control agent 6a. 3-(trans-3-methyl-2-propenoyl)-4-(R)-phenyl-2-oxazolidinone trans-Crotonoyl chloride (2.67 g, 10.24 mmol, Aldrich) was coupled with (R)-4-phenyl-2-oxazolidinone (1.46 g, 8.9 mmol) according to the procedure of Example 1c to afford the title compound (1.67 g). MS m/z 232 (M+H)$^+$, 249 (M+NH$_4$)$^+$.

6b. 3-(trans-1-benzyl-4-(S)-methyl-3-(S)-pyrrolidinylcarbonyl)-4-(R)-phenyl-2-oxazolidinone The compound from step 6a (232 mg, 1.0 mmol) was reacted with N-benzyl-N-(methoxymethyl)trimethylsilylmethylamine (284 mg, 1.2 mmol) according to the procedure of Example 1d, to afford the title compound (224 mg). MS m/z 365 (M+H)$^+$. NMR (CDCl$_3$) d 7.20–7.40 (10H, m), 5.44 (1H, dd, J=9.0, 4.5 Hz), 4.69 (1H, dd, J=9.0, 9.0 Hz), 4.23 (1H, dd, J=9.3, 4.5 Hz), 3.70 (1H, m), 3.65 (1H, d, J=13.2 Hz), 3.46 (1H, d, J=13.2 Hz), 2.99 (1H, dd, J=9.3, 9.0 Hz), 2.88 (1H, dd, J=7.5, 7.5 Hz), 2.78 (1H, m), 2.67 (1H, dd, J=9.9, 5.4 Hz), 2.15 (1H, dd, J=9.0, 7.5 Hz), 1.07 (3H, d, J=6.9 Hz).

6c. (3S,4S)-trans-4-methyl-3-(BOC-amino)pyrrolidine

Carrying the compound of step 6b forward according to the procedures of Example 1e–1g, the title compound is prepared.

Example 7

Preparation of (3R,4R)-trans-4-ethyl-3-(BOC-amino)pyrrolidine via use of (S)-4-phenyl-2-oxazolidinone as chiral control agent 7a. trans-2-pentenoyl chloride trans-2-Pentenoic acid (10.1 mL, 0.1 mol, Aldrich) was dissolved in toluene (100 mL), and the solution was cooled to 0° C. and flushed with N$_2$. Anhydrous DMF (0.150 mL) was added, followed by oxalyl chloride (17.4 mL, 0.2 mol) dropwise at a rate to maintain internal temperature at <10° C. The mixture was stirred at 0° C. for ½ hour and at room temperature overnight. The solvent was removed under vacuum to give the title compound (2.6 g).

7b. 3-(trans-2-pentenoyl)-4-(S)-phenyl-2-oxazolidinone (S)-(+)-4-Phenyl-2-oxazolidinone (4.0 g, 24 mmol, Aldrich) was dissolved in dry THF (40 mL), and the solution was cooled to −50° C. and flushed with N$_2$. Sodium hexamethyldisilazane (1.0M in THF, 25 mL, 25 mmol) was added slowly with stirring. The compound from step 7a (2.9 g, 24 mmol) was added slowly while maintaining the temperature at −50° C., and the mixture was stirred at this temperature for 1.5 hour. The mixture was allowed to warm to 0° C. and stirred for 1 hour. Saturated aqueous NH$_4$Cl solution was added, the mixture was stirred for 10 minutes and the mixture was extracted with methylene chloride. The extract was dried over Na$_2$SO$_4$, filtered and the solvent was removed. The residue was chromatographed on silica gel, eluting with 2% methanol/methylene chloride, and the product was rechromatographed with 0.5% methanol/methylene chloride to give the title compound (1.69 g). MS m/z 246 (M+H)$^+$, 263 (M+NH4)$^+$.

7c. 3-(trans-1-benzyl-4-ethyl-3-pyrrolidinylcarbonyl)-4-(S)-phenyl-2-oxazolidinone The compound from step 7b (490 mg, 2 mmol) was dissolved in methylene chloride (9 mL), and the solution was cooled to 0° C. and flushed with N$_2$. N-benzyl-N-(methoxymethyl)trimethylsilylmethyl-amine (498 mg, 2.1 mmol) was added, the mixture was stirred for 20 minutes and trifluoroacetic acid (1M, 0.2 mL, 0.20 mmol) was added dropwise over 20 minutes with stirring at 0° C. The mixture was stirred at 0° C. for 1 hour and at room temperature for 24 hours, then diluted with 50 mL of methylene chloride, washed with 10% aqueous K$_2$CO$_3$ and dried over Na$_2$SO$_4$. The solvent was removed and the residue was dried under vacuum (767 mg). The isomers were separated by medium pressure liquid chromatography on silica gel, eluting with 0.5% methanol/methylene chloride. The major isomer (3R, 4R) (290 mg) was taken to the next step. MS m/z 379 (M+H)$^+$.

7d. (3R,4R)-trans-4-ethyl-3-(BOC-amino)pyrrolidine

Carrying the compound of step 7c forward according to the procedures of Example 1e–1g, the title compound is prepared.

Example 8

Preparation of (3R,4R)-trans-4-phenyl-3-(BOC-amino)pyrrolidine via use of (S)-4-phenyl-2-oxazolidinone as chiral control agent 8a. trans-cinnamoyl chloride trans-Cinnamic acid (5 g, 33.7 mmol, Aldrich) was dissolved in toluene (100 mL), and the solution was cooled to 0° C. and flushed with N$_2$. Anhydrous DMF (0.1 mL) was added, followed by oxalyl chloride (8.56 g, 5.88 mL, 67.4 mmol) dropwise over 8 minutes. The mixture was stirred at 0° C. for 1 hour and at room temperature for 1.5 hours. The solvent was removed under vacuum to give the title compound (7.63 g).

8b. 3-(trans-cinnamoyl)-4-(S)-phenyl-2-oxazolidinone (S)-(+)-4-Phenyl-2-oxazolidinone (4.77 g, 29.3 mmol, Aldrich) was dissolved in dry THF (100 mL), and the solution was cooled to −78° C. and flushed with N$_2$. n-Butyllithium (2.5M in THF, 11.7 mL, 29.3 mmol) was introduced over 10 minutes. The compound from step 8a (in 30 mL of THF) was added over 10 minutes, and the mixture was stirred at −78° C. for half an hour. The mixture was stirred as it was allowed to warm to room temperature. Saturated aqueous NH$_4$Cl solution was added, the mixture was stirred for 10 minutes and the THF was removed under reduced pressure. The residue was dissolved in ethyl acetate, and the solution was washed with water, 5% aqueous NaHCO$_3$ and brine, then dried over Na$_2$SO$_4$. The solvent was removed to afford the title compound, which was recrystallized from ethyl acetate to give the title product (7.18 g). MS m/z 294 (M+H)$^+$, 311 (M+NH$_4$)$^+$.

8c. 3-(trans-1-benzyl-4-phenyl-3-pyrrolidinylcarbonyl)-4-(S)-phenyl-2-oxazolidinone The compound from step 8b (294 mg, 1.2 mmol) was dissolved in toluene (10 mL), and the solution flushed with N$_2$. N-benzyl-N-(methoxymethyl)trimethylsilylmethylamine (284 mg, 0.227 mmol) was added, the mixture was stirred for 20 minutes and trifluoroacetic acid (1M, 0.1 mL, 0.10 mmol) was added dropwise. The mixture was stirred for 1.5 hour at room temperature, then diluted with 50 mL of ethyl acetate, washed with 5% aqueous NaHCO$_3$ and dried over Na$_2$SO$_4$. The solvent was removed and the residue was dried under vacuum (542 mg). The isomers were separated by chromatography on silica gel, and the major isomer (3R,4R) was taken to the next step. MS m/z 427 (M+H)⁺.

8d. (3R,4R)-trans-4-phenyl-3-(BOC-amino)pyrrolidine

Carrying the compound of step 7c forward according to the procedures of Example 1e–1g, the title compound is prepared.

We claim:

1. A compound selected from the group consisting of

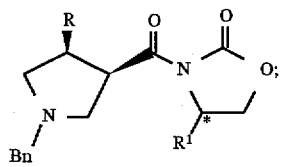
(a)

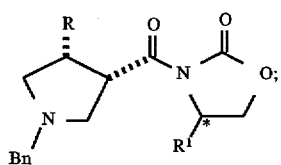
(b)

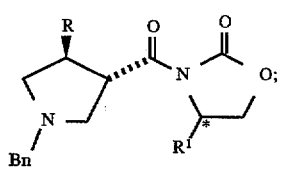
(c)

and

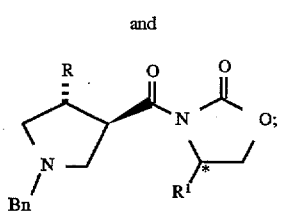
(d)

wherein * represents a chiral center, Bn is benzyl, R is selected from the group consisting of $C_1$–$C_6$-alkyl, $C_3$–$C_5$-cycloalkyl, phenyl and phenyl-substituted-$C_1$–$C_6$-alkyl, and $R^1$ is selected from the group consisting of isopropyl, isobutyl, t-butyl, phenyl, benzyl, 1-phenylethyl, diphenylmethyl, naphthyl and adamantyl.

2. A compound according to claim 1, which is selected from the group consisting of:

3-(trans-1-benzyl-4-(S)-cyclopropyl-3-(S)-pyrrolidinylcarbonyl)-4-(R)-phenyl-2-oxazolidinone;
3-(trans-1-benzyl-4-(R)-cyclopropyl-3-(R)-pyrrolidinylcarbonyl)-4-(R)-phenyl-2-oxazolidinone;
3-(trans-1-benzyl-4-(S)-cyclopropyl-3-(S)-pyrrolidinylcarbonyl)-4-(S)-phenyl-2-oxazolidinone;
3-(trans-1-benzyl-4-(R)-cyclopropyl-3-(R)-pyrrolidinylcarbonyl)-4-(S)-phenyl-2-oxazolidinone;
3-(trans-1-benzyl-4-(S)-methyl-3-(S)-pyrrolidinylcarbonyl)-4-(R)-phenyl-2-oxazolidinone;
3-(trans-1-benzyl-4-(R)-methyl-3-(R)-pyrrolidinylcarbonyl)-4-(R)-phenyl-2-oxazolidinone;
3-(trans-1-benzyl-4-(S)-methyl-3-(S)-pyrrolidinylcarbonyl)-4-(S)-phenyl-2-oxazolidinone;
3-(trans-1-benzyl-4-(R)-methyl-3-(R)-pyrrolidinylcarbonyl)-4-(S)-phenyl-2-oxazolidinone;
3-(trans-1-benzyl-4-(S)-ethyl-3-(S)-pyrrolidinylcarbonyl)-4-(R)-phenyl-2-oxazolidinone;
3-(trans-1-benzyl-4-(R)-ethyl-3-(R)-pyrrolidinylcarbonyl)-4-(R)-phenyl-2-oxazolidinone;
3-(trans-1-benzyl-4-(S)-ethyl-3-(S)-pyrrolidinylcarbonyl)-4-(S)-phenyl-2-oxazolidinone;
3-(trans-1-benzyl-4-(R)-ethyl-3-(R)-pyrrolidinylcarbonyl)-4-(S)-phenyl-2-oxazolidinone;
3-(trans-1-benzyl-4-(S)-cyclopropyl-3-(S)-pyrrolidinylcarbonyl)-4-(R)-isopropyl-2-oxazolidinone;
3-(trans-1-benzyl-4-(R)-cyclopropyl-3-(R)-pyrrolidinylcarbonyl)-4-(R)-isopropyl-2-oxazolidinone;
3-(trans-1-benzyl-4-(S)-cyclopropyl-3-(S)-pyrrolidinylcarbonyl)-4-(S)-isopropyl-2-oxazolidinone;
3-(trans-1-benzyl-4-(R)-cyclopropyl-3-(R)-pyrrolidinylcarbonyl)-4-(S)-isopropyl-2-oxazolidinone;
3-(trans-1-benzyl-4-(S)-methyl-3-(S)-pyrrolidinylcarbonyl)-4-(R)-isopropyl-2-oxazolidinone;
3-(trans-1-benzyl-4-(R)-methyl-3-(R)-pyrrolidinylcarbonyl)-4-(R)-isopropyl-2-oxazolidinone;
3-(trans-1-benzyl-4-(S)-methyl-3-(S)-pyrrolidinylcarbonyl)-4-(S)-isopropyl-2-oxazolidinone;
3-(trans-1-benzyl-4-(R)-methyl-3-(R)-pyrrolidinylcarbonyl)-4-(S)-isopropyl-2-oxazolidinone;
3-(trans-1-benzyl-4-(S)-ethyl-3-(S)-pyrrolidinylcarbonyl)-4-(R)-isopropyl-2-oxazolidinone;
3-(trans-1-benzyl-4-(R)-ethyl-3-(R)-pyrrolidinylcarbonyl)-4-(R)-isopropyl-2-oxazolidinone;
3-(trans-1-benzyl-4-(S)-ethyl-3-(S)-pyrrolidinylcarbonyl)-4-(S)-isopropyl-2-oxazolidinone;
3-(trans-1-benzyl-4-(R)-ethyl-3-(R)-pyrrolidinylcarbonyl)-4-(S)-isopropyl-2-oxazolidinone;
3-(trans-1-benzyl-4-(S)-cyclopropyl-3-(S)-pyrrolidinylcarbonyl)-4-(R)-benzyl-2-oxazolidinone;
3-(trans-1-benzyl-4-(R)-cyclopropyl-3-(R)-pyrrolidinylcarbonyl)-4-(R)-benzyl-2-oxazolidinone;
3-(trans-1-benzyl-4-(S)-cyclopropyl-3-(S)-pyrrolidinylcarbonyl)-4-(S)-benzyl-2-oxazolidinone;
3-(trans-1-benzyl-4-(R)-cyclopropyl-3-(R)-pyrrolidinylcarbonyl)-4-(S)-benzyl-2-oxazolidinone;
3-(trans-1-benzyl-4-(S)-methyl-3-(S)-pyrrolidinylcarbonyl)-4-(R)-benzyl-2-oxazolidinone;
3-(trans-1-benzyl-4-(R)-methyl-3-(R)-pyrrolidinylcarbonyl)-4-(R)-benzyl-2-oxazolidinone;
3-(trans-1-benzyl-4-(S)-methyl-3-(S)-pyrrolidinylcarbonyl)-4-(S)-benzyl-2-oxazolidinone;
3-(trans-1-benzyl-4-(R)-methyl-3-(R)-pyrrolidinylcarbonyl)-4-(S)-benzyl-2-oxazolidinone;
3-(trans-1-benzyl-4-(S)-ethyl-3-(S)-pyrrolidinylcarbonyl)-4-(R)-benzyl-2-oxazolidinone;
3-(trans-1-benzyl-4-(R)-ethyl-3-(R)-pyrrolidinylcarbonyl)-4-(R)-benzyl-2-oxazolidinone;
3-(trans-1-benzyl-4-(S)-ethyl-3-(S)-pyrrolidinylcarbonyl)-4-(S)-benzyl-2-oxazolidinone;
3-(trans-1-benzyl-4-(R)-ethyl-3-(R)-pyrrolidinylcarbonyl)-4-(S)-benzyl-2-oxazolidinone;
3-(cis-1-benzyl-4-(S)-cyclopropyl-3-(R)-pyrrolidinylcarbonyl)-4-(R)-phenyl-2-oxazolidinone;
3-(cis-1-benzyl-4-(R)-cyclopropyl-3-(S)-pyrrolidinylcarbonyl)-4-(R)-phenyl-2-oxazolidinone;
3-(cis-1-benzyl-4-(S)-cyclopropyl-3-(R)-pyrrolidinylcarbonyl)-4-(S)-phenyl-2-oxazolidinone;
3-(cis-1-benzyl-4-(R)-cyclopropyl-3-(S)-pyrrolidinylcarbonyl)-4-(S)-phenyl-2-oxazolidinone;
3-(cis-1-benzyl-4-(S)-methyl-3-(R)-pyrrolidinylcarbonyl)-4-(R)-phenyl-2-oxazolidinone;
3-(cis-1-benzyl-4-(R)-methyl-3-(S)-pyrrolidinylcarbonyl)-4-(R)-phenyl-2-oxazolidinone;
3-(cis-1-benzyl-4-(S)-methyl-3-(R)-pyrrolidinylcarbonyl)-4-(S)-phenyl-2-oxazolidinone;
3-(cis-1-benzyl-4-(R)-methyl-3-(S)-pyrrolidinylcarbonyl)-4-(S)-phenyl-2-oxazolidinone;
3-(cis-1-benzyl-4-(S)-ethyl-3-(R)-pyrrolidinylcarbonyl)-4-(R)-phenyl-2-oxazolidinone;

3-(cis-1-benzyl-4-(R)-ethyl-3-(S)-pyrrolidinylcarbonyl)-4-(R)-phenyl-2-oxazolidinone;
3-(cis-1-benzyl-4-(S)-ethyl-3-(R)-pyrrolidinylcarbonyl)-4-(S)-phenyl-2-oxazolidinone;
3-(cis-1-benzyl-4-(R)-ethyl-3-(S)-pyrrolidinylcarbonyl)-4-(S)-phenyl-2-oxazolidinone;
3-(cis-1-benzyl-4-(S)-cyclopropyl-3-(R)-pyrrolidinylcarbonyl)-4-(R)-isopropyl-2-oxazolidinone;
3-(cis-1-benzyl-4-(R)-cyclopropyl-3-(S)-pyrrolidinylcarbonyl)-4-(R)-isopropyl-2-oxazolidinone;
3-(cis-1-benzyl-4-(S)-cyclopropyl-3-(R)-pyrrolidinylcarbonyl)-4-(S)-isopropyl-2-oxazolidinone;
3-(cis-1-benzyl-4-(R)-cyclopropyl-3-(S)-pyrrolidinylcarbonyl)-4-(S)-isopropyl-2-oxazolidinone;
3-(cis-1-benzyl-4-(S)-methyl-3-(R)-pyrrolidinylcarbonyl)-4-(R)-isopropyl-2-oxazolidinone;
3-(cis-1-benzyl-4-(R)-methyl-3-(S)-pyrrolidinylcarbonyl)-4-(R)-isopropyl-2-oxazolidinone;
3-(cis-1-benzyl-4-(S)-methyl-3-(R)-pyrrolidinylcarbonyl)-4-(S)-isopropyl-2-oxazolidinone;
3-(cis-1-benzyl-4-(R)-methyl-3-(S)-pyrrolidinylcarbonyl)-4-(S)-isopropyl-2-oxazolidinone;
3-(cis-1-benzyl-4-(S)-ethyl-3-(R)-pyrrolidinylcarbonyl)-4-(R)-isopropyl-2-oxazolidinone;
3-(cis-1-benzyl-4-(R)-ethyl-3-(S)-pyrrolidinylcarbonyl)-4-(R)-isopropyl-2-oxazolidinone;
3-(cis-1-benzyl-4-(S)-ethyl-3-(R)-pyrrolidinylcarbonyl)-4-(S)-isopropyl-2-oxazolidinone;
3-(cis-1-benzyl-4-(R)-ethyl-3-(S)-pyrrolidinylcarbonyl)-4-(S)-isopropyl-2-oxazolidinone;
3-(cis-1-benzyl-4-(S)-cyclopropyl-3-(R)-pyrrolidinylcarbonyl)-4-(R)-benzyl-2-oxazolidinone;
3-(cis-1-benzyl-4-(R)-cyclopropyl-3-(S)-pyrrolidinylcarbonyl)-4-(R)-benzyl-2-oxazolidinone;
3-(cis-1-benzyl-4-(S)-cyclopropyl-3-(R)-pyrrolidinylcarbonyl)-4-(S)-benzyl-2-oxazolidinone;
3-(cis-1-benzyl-4-(R)-cyclopropyl-3-(S)-pyrrolidinylcarbonyl)-4-(S)-benzyl-2-oxazolidinone;
3-(cis-1-benzyl-4-(S)-methyl-3-(R)-pyrrolidinylcarbonyl)-4-(R)-benzyl-2-oxazolidinone;
3-(cis-1-benzyl-4-(R)-methyl-3-(S)-pyrrolidinylcarbonyl)-4-(R)-benzyl-2-oxazolidinone;
3-(cis-1-benzyl-4-(S)-methyl-3-(R)-pyrrolidinylcarbonyl)-4-(S)-benzyl-2-oxazolidinone;
3-(cis-1-benzyl-4-(R)-methyl-3-(S)-pyrrolidinylcarbonyl)-4-(S)-benzyl-2-oxazolidinone;
3-(cis-1-benzyl-4-(S)-ethyl-3-(R)-pyrrolidinylcarbonyl)-4-(R)-benzyl-2-oxazolidinone;
3-(cis-1-benzyl-4-(R)-ethyl-3-(S)-pyrrolidinylcarbonyl)-4-(R)-benzyl-2-oxazolidinone;
3-(cis-1-benzyl-4-(S)-ethyl-3-(R)-pyrrolidinylcarbonyl)-4-(S)-benzyl-2-oxazolidinone; and
3-(cis-1-benzyl-4-(R)-ethyl-3-(S)-pyrrolidinylcarbonyl)-4-(S)-benzyl-2-oxazolidinone.

* * * * *